(12) United States Patent
Kim et al.

(10) Patent No.: US 10,130,392 B2
(45) Date of Patent: Nov. 20, 2018

(54) STRUCTURE HAVING VARIABLE DIAMETER

(71) Applicant: KCIS CO., LTD., Goyang-si, Gyeonggi-do (KR)

(72) Inventors: Doo Man Kim, Gwangmyeong-si (KR); Gwang Won Kim, Gyeonggi-Si (KR)

(73) Assignee: Doo Man Kim, Gwangmyeong-si (KR)

( * ) Notice: Subject to any disclaimer, the term of this patent is extended or adjusted under 35 U.S.C. 154(b) by 0 days.

(21) Appl. No.: 15/543,509

(22) PCT Filed: Jan. 12, 2016

(86) PCT No.: PCT/KR2016/000301
§ 371 (c)(1),
(2) Date: Jul. 13, 2017

(87) PCT Pub. No.: WO2016/114558
PCT Pub. Date: Jul. 21, 2016

(65) Prior Publication Data
US 2017/0348022 A1    Dec. 7, 2017

(30) Foreign Application Priority Data

Jan. 14, 2015   (KR) .................. 10-2015-0006757
Jan. 12, 2016   (KR) .................. 10-2016-0003471

(51) Int. Cl.
*A61B 17/68*    (2006.01)
*A61B 17/70*    (2006.01)
*A61B 17/72*    (2006.01)

(52) U.S. Cl.
CPC .......... *A61B 17/68* (2013.01); *A61B 17/7013* (2013.01); *A61B 17/7233* (2013.01); *A61B 17/7258* (2013.01)

(58) Field of Classification Search
CPC . A61B 17/68; A61B 17/7013; A61B 17/7233; A61B 17/7208; A61B 17/7266; A61B 17/7291; A61B 17/1717; A61B 17/1725; A61B 17/7283; A61B 17/744; A61B 17/746
USPC ................. 606/62–68, 300–328, 246–279
See application file for complete search history.

(56) References Cited

U.S. PATENT DOCUMENTS

| | | | |
|---|---|---|---|
| 6,736,818 B2 | 5/2004 | Perren et al. | |
| 7,601,152 B2* | 10/2009 | Levy | A61B 17/7266 606/62 |
| 7,670,339 B2 | 3/2010 | Levy et al. | |
| 8,545,499 B2 | 10/2013 | Lozier et al. | |

(Continued)

*Primary Examiner* — Pedro Philogene
(74) *Attorney, Agent, or Firm* — Weitzman Law Offices, LLC

(57) ABSTRACT

The present invention relates to a structure having a variable diameter, the structure including: a bolt which extends in a longitudinal direction; a body which is disposed at one side of the bolt so as to surround the bolt; a core which is disposed in the longitudinal direction of the bolt; a plurality of extensions which is radially disposed outside the core; and a plurality of outer shells which surrounds the extensions so as to correspond to the extensions, in which the extensions are expanded outward or contracted in a direction toward a center thereof by the core in accordance with a rotation direction of the bolt, such that a diameter of an outer circumferential surface of the extensions is changed.

9 Claims, 4 Drawing Sheets

(56) References Cited

U.S. PATENT DOCUMENTS

| | | | |
|---|---|---|---|
| 8,840,612 B2* | 9/2014 | Tontz | A61B 17/7258 |
| | | | 606/63 |
| 2008/0287951 A1 | 11/2008 | Stoneburner et al. | |
| 2013/0116693 A1* | 5/2013 | Nelson | A61B 17/7233 |
| | | | 606/64 |

* cited by examiner (a)

(b)

STRUCTURE HAVING VARIABLE DIAMETER

TECHNICAL FIELD

The present invention relates to a structure having a variable diameter, and more particularly, to a structure having a variable diameter which is increased and decreased in accordance with a rotation direction of a screw, such that the structure may be fixedly inserted into a part so as to correspond to the part even though the part has a relatively large diameter and the structure may be easily removed.

BACKGROUND ART

To connect structures such as a hollow shaft or a pipe having a doughnut shape and inner and outer diameters, a separate connecting bracket, which surrounds an outer portion of the structure or is inserted into an inner portion of the structure, is necessarily required.

However, in the related art, the connecting bracket generally needs to necessarily coincide with the outer or inner diameter, and as a result, there is a problem in that the connecting brackets, which correspond to varying diameters, are required.

In addition, products such as shaft pins, which are fastened in an interference fit manner, also need to be installed after being manufactured to have a size corresponding to the diameter, and as a result, it is difficult to manufacture the product.

DISCLOSURE

[Technical Problem]

The present invention has been made in an effort to improve properties of the structure in the related art, and an object of the present invention is to provide a structure having a variable diameter which is increased and decreased in accordance with a rotation direction of a screw, such that the structure may be fixedly inserted into a part so as to correspond to the part even though the part has a relatively large diameter and the structure may be easily removed.

[Technical Solution]

The present invention has the following configuration to achieve the aforementioned object.

A structure having a variable diameter according to the present invention includes: a bolt which extends in a longitudinal direction; a body which is disposed at one side of the bolt so as to surround the bolt; a core which is disposed in the longitudinal direction of the bolt; a plurality of extensions which is radially disposed outside the core; and a plurality of outer shells which surrounds the extensions so as to correspond to the extensions, in which the extensions are expanded outward or contracted in a direction toward a center thereof by the core in accordance with a rotation direction of the bolt, such that a diameter of an outer circumferential surface of the extensions is changed.

Further, the body may include an insertion hole into which the bolt is inserted, and guide grooves which are connected to ends of the extensions and radially guide the extensions.

In addition, the core may include a cylindrical body which has a screw hole, a plurality of slot members which radially extends from an outer circumferential surface of the cylindrical body, and slot protrusions which protrude between the slot members so as to face each other, and the core may increase or decrease the outer diameter of the extensions.

Further, the slot protrusion may be disposed to be inclined outward with respect to an axial direction of the bolt.

Further, the extension may have a predetermined length, and may include a guide protrusion which is formed at an end portion in the longitudinal direction of the extension, slots which are formed to be inclined at both sides in the longitudinal direction and guide the sliding movement of the slot protrusions, a wedge groove which is formed at a position orthogonal to the slots and recessed in the longitudinal direction, and wedge catching protrusions which are formed to face each other at one side of the wedge groove so that a portion between the wedge catching protrusions becomes narrow.

Further, the extension may be formed to be relatively longer than a length of the core.

Further, the outer shells may be disposed to overlap one another.

Further, a plurality of spacers may be further provided on the bolt so that a plurality of cores is installed.

Meanwhile, the structure of the present invention may be used to connect structural bodies which have a doughnut-shaped cross section and a predetermined inner diameter.

[Advantageous Effects]

According to the present invention, the diameter of the structure is increased and decreased in accordance with the rotation direction of the screw, such that the structure may be fixedly inserted into a part so as to correspond to the part even though the part has a relatively large diameter and the structure may be easily removed.

In addition, the structure according to the present invention may be used as a nail for connecting a fractured bone.

MODES OF THE INVENTION

Figure 1:
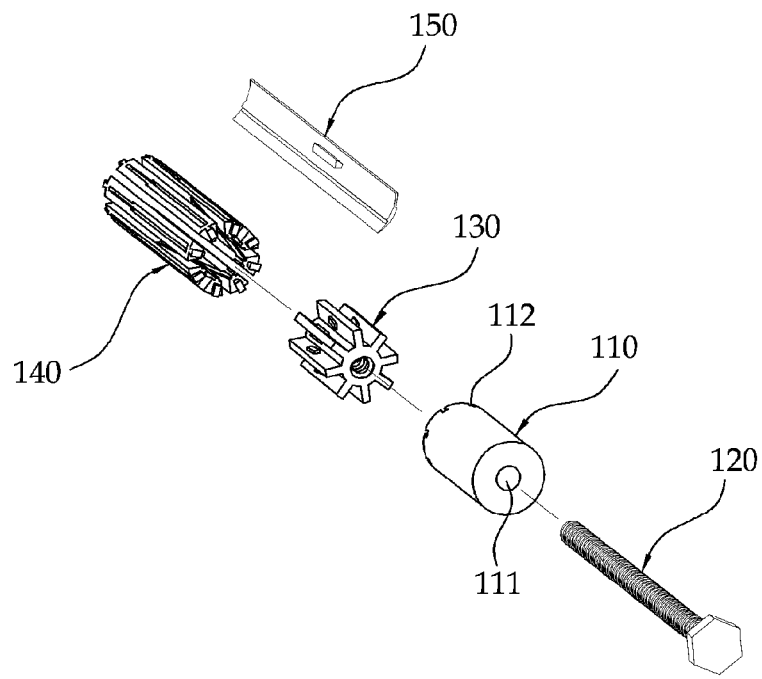
FIG. 1 is an exploded perspective view illustrating a structure having a variable diameter of the present invention.

The aforementioned objects, features and advantages of the present invention will become more apparent from the following exemplary embodiments related to the accompanying drawings.

The following descriptions of specific structures and functions are exemplified only for explaining the exemplary embodiments according to the concept of the present invention, and the exemplary embodiments according to the concept of the present invention may be embodied in various forms and should not be construed as being limited to the exemplary embodiments described in the present specification.

The exemplary embodiments according to the concept of the present invention may be changed in various forms and may include various forms, such that specific exemplary embodiments will be illustrated in the drawings and described in detail in the present specification. However, the description is not intended to limit the exemplary embodiments according to the concept of the present invention to the specific disclosed forms, and it is to be understood that all the changes, equivalents, and substitutions belonging to the spirit and technical scope of the present invention are included in the present invention.

The terms such as "first" and/or "second" may be used to describe various constituent elements, but the constituent elements are not limited to the terms. The terms are used only for the purpose of differentiating one constituent element from the other constituent elements, and for example, a first component may be named a second component and similarly, the second component may also be named the first component, without departing from the scope according to the concept of the present invention.

When one constituent element is described as being "connected" or "coupled" to another constituent element, it should be understood that one constituent element can be connected or coupled directly to another constituent element, and an intervening constituent element can also be present between the constituent elements. When one constituent element is described as being "connected directly to" or "coupled directly to" another constituent element, it should be understood that no intervening constituent element is present between the constituent elements. Other expressions for explaining relationships between constituent elements, that is, the expressions such as "between" and "right between", or "adjacent to" and "adjacent directly to" should be construed similarly.

Terms used in the present specification are used only to describe specific exemplary embodiments, and are not intended to limit the present invention. Singular expressions used herein include plurals expressions unless they have definitely opposite meanings in the context. In the present application, it will be appreciated that terms "including" and "having" are intended to designate the existence of characteristics, numbers, steps, operations, constituent elements, and components described in the specification or a combination thereof, and do not exclude a possibility of the existence or addition of one or more other characteristics, numbers, steps, operations, constituent elements, and components, or a combination thereof in advance.

All terms used herein including technical or scientific terms have the same meanings as meanings which are generally understood by those skilled in the technical field to which the present invention pertains unless they are differently defined. Terms defined in a generally used dictionary shall be construed that they have meanings matching those in the context of a related art, and shall not be construed in ideal or excessively formal meanings unless they are clearly defined in the present specification.

As illustrated in FIG. 1, a structure having a variable diameter of the present invention includes a body 110, a bolt 120, a core 130, extensions 140, and outer shells 150.

The body 110 has an insertion groove 111 which penetrates a center of a cylindrical shape in an axial direction, and guide grooves 112 which are formed at an equal interval around an one end portion in the axial direction, and the guide groove 112 has a tapered shape of which the width is increased toward the inside of the body 110.

The bolt 120 has a predetermined length, and a screw thread is formed in a trapezoidal shape on an outer circumferential surface of the bolt 120.

Figure 2:
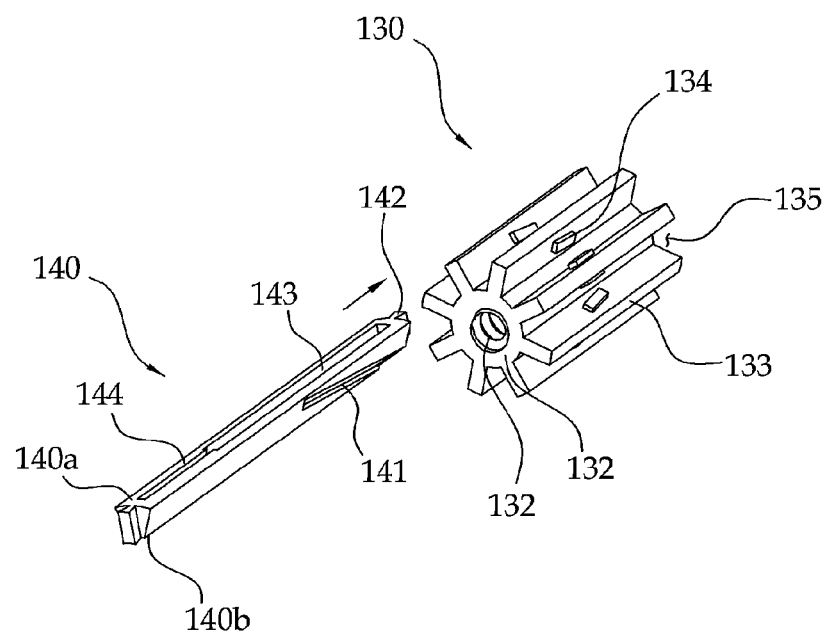
FIG. 2 is a perspective view illustrating a core and an extension illustrated in FIG. 1.

As illustrated in FIG. 2, the core 130 includes a cylindrical body 131 which has a screw hole 132 formed in the axial direction at a center of the cylindrical body 131 so that the bolt 120 may be fastened to the screw hole 132, a plurality of slot members 133 which has the same length as the cylindrical body 131 and radially extends from an outer circumferential surface of the cylindrical body 131, slot protrusions 134 which protrude to face each other on lateral surfaces of the slot members 133, and insertion grooves 135 which are formed between slot members 133 so that the extensions 140 are positioned in the insertion grooves 135.

The slot protrusion 134 is disposed to be inclined outward with respect to the axial direction.

The extension 140 is inserted into the insertion groove 135 between the slot members 133 and operates in the insertion groove 135, and the extension 140 includes slots 141 which are formed to be inclined in both surfaces in a longitudinal direction, guide protrusions 142 which protrude at both ends in the longitudinal direction, a wedge groove 143 which is formed in an upper surface of the extension 140 in the longitudinal direction and recessed to a predetermined depth, and wedge catching protrusions 144 which extend and protrude inside the wedge groove 143 so as to face each other.

Figure 3:
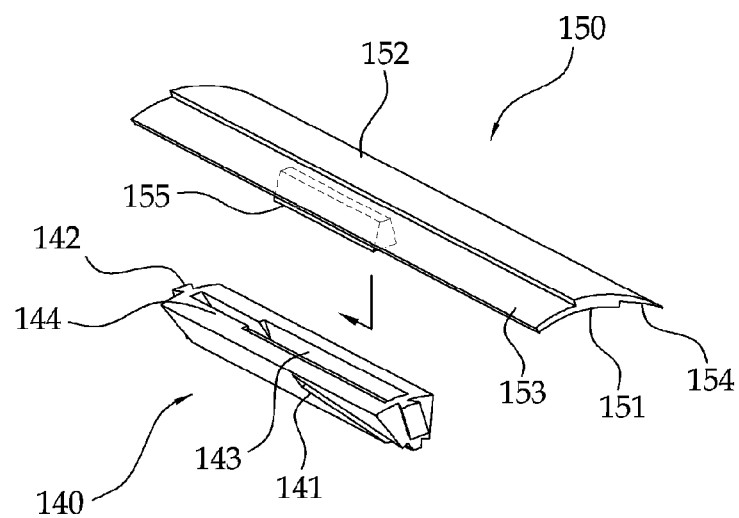
FIG. 3 is a perspective view illustrating the extension and an outer shell illustrated in FIG. 1.
Figure 3:
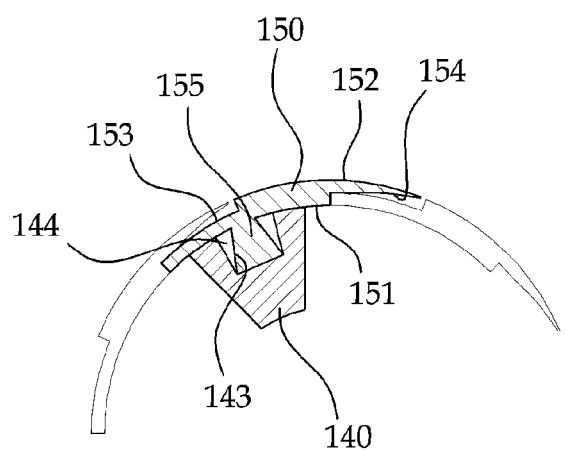

As illustrated in FIG. 3B, the wedge catching protrusion 144 is inclined outward from a bottom surface of the wedge groove 143, and an upper surface 140a and a lower surface 140b of the extension 140 have a curved shape.

As illustrated in FIG. 3A, the outer shell 150 has a curved shape having a predetermined length, and includes a wedge 155 protruding downward from a bottom surface 151 of the outer shell 150.

In addition, the outer shell 150 has a lower overlapping surface 154 which is formed at one side of the outer shell 150 so as to be stepped with respect to the bottom surface 155, and an upper overlapping surface 153 which is formed on an upper portion formed diagonally to the lower overlapping surface 154 so as to be stepped with respect to an outer surface 152.

That is, as illustrated in FIG. 3B, the plurality of outer shells overlaps one another to define an outermost periphery of the structure, and a degree to which the plurality of outer shells overlaps one another is changed as a diameter of an outer circumference of the structure is changed, such that the plurality of outer shells may come into close contact with a structural body into which the structure is inserted.

In a coupled state in the present invention, the bolt 120 is inserted into the insertion hole 111 of the body 110 first, and then the screw hole 132 of the core 130 is thread-coupled to the bolt 130.

Thereafter, the plurality of extensions 140 is positioned in the insertion grooves 135 of the core 130, respectively, the slot protrusions 134 are inserted into the slots 141, and the guide protrusions 142 are inserted into the guide grooves 112 of the body 110.

That is, the extensions 140 are disposed at an equal interval along an outer circumference of the core 130.

In this state, the wedges 155 of the outer shells 150 are inserted into the wedge grooves 143 formed in the upper surfaces 140a of the extensions 140, such that the wedges 155 are pressed against the wedge catching protrusions 144, and the wedges 155 are caught by and coupled to the wedge catching protrusions 144.

In this case, when the outer shells 150 are coupled to the extensions 140, the lower overlapping surfaces 154 of the outer shells 150 overlap the upper overlapping surfaces 153 of the neighboring outer shells, such that the lower overlapping surfaces 154 and the upper overlapping surfaces 153 slide relative to one another when the extensions are expanded and contracted, and as a result, the cylindrical shape may be maintained, and the structure may come into close contact with an inner portion of the structural body.

Figure 4:
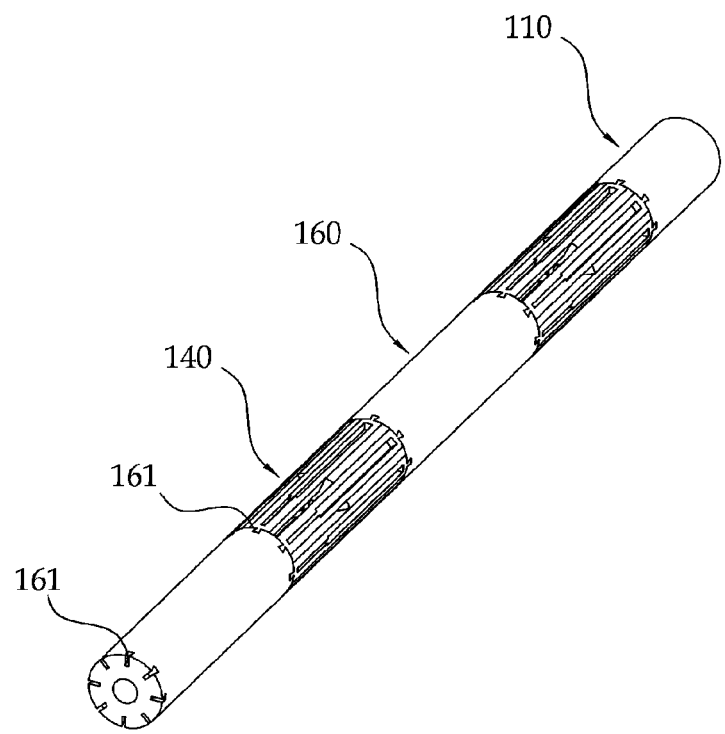
FIG. 4 is a view illustrating a state in which the structure having a variable diameter according to the present invention has spacers.

Meanwhile, in the present invention, a configuration in which the extensions are installed on the single core is described, but as illustrated in FIG. 4, a spacer 160, which has the guide grooves 161 formed at both ends of the spacer 160 in the longitudinal direction, may be provided, and the plurality of cores may be continuously connected and used, and although not illustrated in the drawings, a separate triangular cone may be disposed at an end portion of the spacer 160 so that the structure is easily inserted into the inner portion of the structural body.

Hereinafter, an operation state of the present invention will be described with reference to the accompanying drawings.

First, the structure of the present invention may be disposed in a state in which an outer side of the body 110 and an inner side of the outer shell 150 are spaced apart from each other at a predetermined interval.

Figure 5:
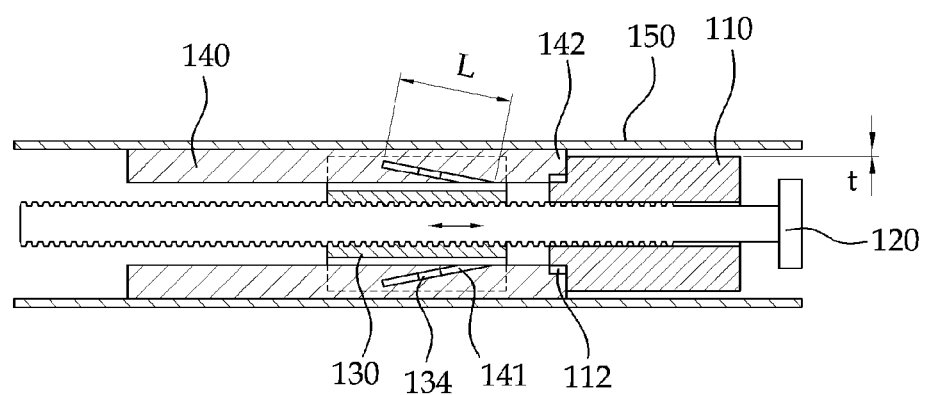
FIGS. 5 to 8 are views illustrating an operation state of the structure having a variable diameter according to the present invention.

That is, as illustrated in FIG. 5, the slot protrusion 134 is positioned at a central portion of the slot 141 based on an overall length L of the slot 141 so that a gap t is formed between the inner side of the outer shell 150 and the outer side of the body 110. In accordance with a rotation direction of the bolt 120, the core 130 is moved forward or rearward in the axial direction of the bolt 120, the slot protrusions 134 of the cores slide forward or rearward along the slots 141, the extensions 140 connected to the core are contracted inward or expanded, and a diameter of the outer shells disposed at the outermost periphery is decreased or increased, thereby easily corresponding to the inner diameter of the structural body.

In this case, the slot protrusions 134 and the slots 141 are disposed to be inclined outward.

A state in which the outer diameter is decreased will be described with reference to FIG. 6. When the bolt 120 is rotated in a direction of the arrow in the drawing, the screw hole 131 of the core 130 is moved forward in the axial direction of the bolt 120 (the direction of the arrow) by the screw thread of the bolt, and the slot protrusions 134 inserted into the slot 141 are moved inclinedly along the slot 141 during the process in which the screw hole 131 of the core 130 is moved forward.

The extensions 140 are moved inward by the slot protrusions 134 being moved inclinedly, and the outer diameter "D" of the outer shells 150 connected to the extensions 140 is decreased to an outer diameter "D1".

In this case, since the guide protrusions 142 of the extensions 140 are inserted into the guide grooves 112 of the body 110, the guide protrusions 142 guide the extensions while supporting the extensions on the body in a direction orthogonal to the axial direction.

That is, the slots 141, which are disposed to be inclined, slide along the slot protrusions 134 as the core 130 is moved along the bolt 120, and the slots 141 are moved inward along the slot protrusions 134, and as a result, the diameter of the outer shells is decreased.

Figure 6:
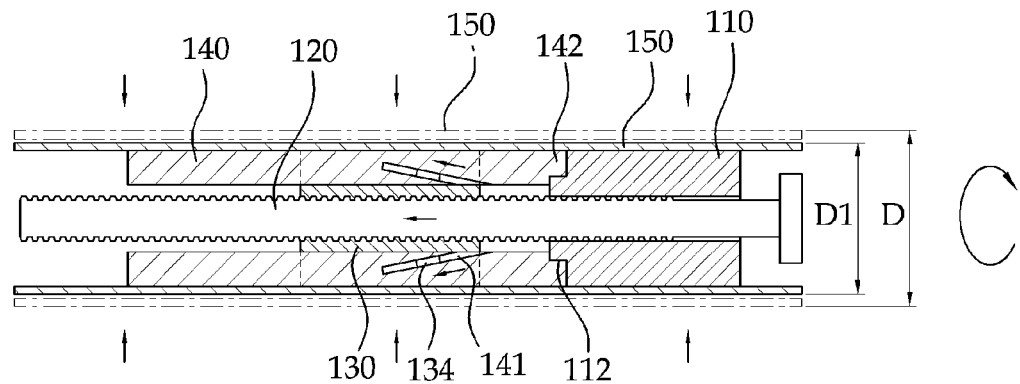
Figure 7:
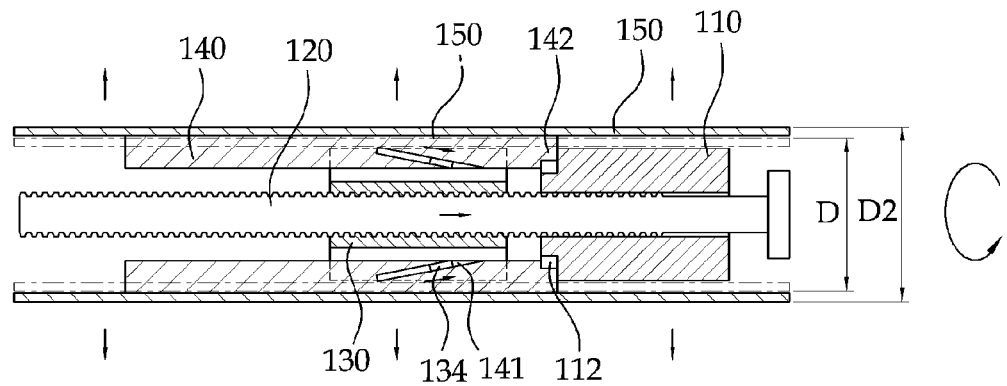

On the contrary, as illustrated in FIG. 7, to increase the outer diameter "D" of the outer shells, when the bolt 120 is rotated in a direction opposite to the direction in which the bolt is rotated in FIG. 6, the core 130 is moved rearward (the direction of the arrow) along the bolt 130 so as to become close to the body 110, and the slot protrusions 134 slide along the slots 141.

As the slot protrusions 134 slide along the slots 141, the extensions 140 having the inclined slots 141 are moved outward, and at the same time, the outer diameter "D" of the outer shells 150 connected to the extensions 140 is increased to an outer diameter "D2".

In this case, since the guide protrusions 142 of the extensions 140 are inserted into the guide grooves 112 of the body 110, the guide protrusions 142 guide the extensions while supporting the extensions on the body in the direction orthogonal to the axial direction.

Figure 8:
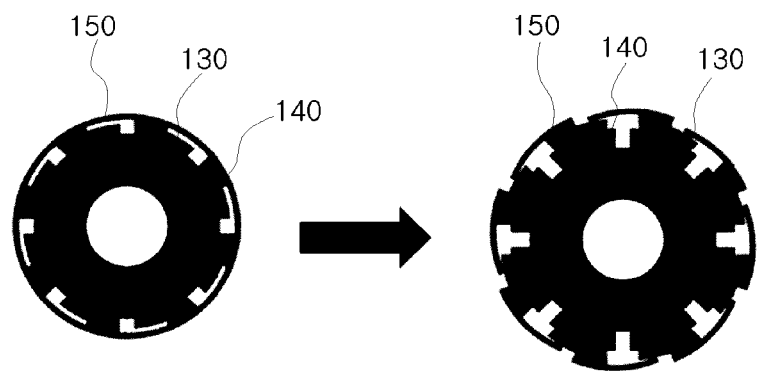

In addition, as illustrated in FIG. 8, since the outer shells are disposed to overlap one another, it is possible to prevent a gap from being formed when the outer diameter is increased or decreased, and it is possible to allow an outer portion of the structure to come into close contact with the inner portion of the structural body.

The structure, which has the outer diameter that may be decreased and increased like the structure of the present invention, may be very usefully used to connect or disconnect pipes having a doughnut-shaped cross section since the structure may be freely attached and detached because of the variable diameter of the structure, thereby greatly reducing operating costs. In particular, in a case in which the structure is used as a nail used to connect fractured bones during a surgical operation, the surgical operation can be effectively carried out because it is possible to prevent the occurrence of impact that may be applied to the bones when the nail is inserted.

While the present invention has been described with reference to the exemplary embodiments, but the exemplary embodiments are provided for better understanding of the technical contents of the present invention, and are not intended to limit the scope of the present invention.

That is, the exemplary embodiments can be variously modified and altered by those skilled in the art without departing from the subject matter of the present invention, and of course, the modification and alteration belong to the technical scope of the present invention in view of the claims.

The invention claimed is:

1. A structure having a variable diameter, the structure comprising:
   a bolt which extends in a longitudinal direction;
   a body which is disposed at one side of the bolt so as to surround the bolt;
   a core which is disposed in the longitudinal direction of the bolt;
   a plurality of extensions which is radially disposed outside the core; and
   a plurality of outer shells which surrounds the extensions so as to correspond to the extensions,
   wherein the extensions are expanded outward or contracted in a direction toward a center thereof by the core in accordance with a rotation direction of the bolt, such that a diameter of an outer circumferential surface of the extensions is changed.

2. The structure of claim 1, wherein the body includes an insertion hole into which the bolt is inserted and guide grooves which are connected to ends of the extensions and radially guide the extensions.

3. The structure of claim 1, wherein the core includes a cylindrical body which has a screw hole, a plurality of slot members which radially extends from an outer circumferential surface of the cylindrical body, and slot protrusions which protrude between the slot members so as to face each other, and the core increases or decreases the outer diameter of the extensions.

4. The structure of claim 3, wherein the slot protrusion is disposed to be inclined outward with respect to an axial direction of the bolt.

5. The structure of claim 3, wherein the extension has a predetermined length, and includes a guide protrusion which is formed at an end portion in the longitudinal direction of the extension, slots which are formed to be inclined at both sides in the longitudinal direction and guide the sliding movement of the slot protrusions, a wedge groove which is formed at a position orthogonal to the slots and recessed in the longitudinal direction, and wedge catching protrusions which are formed to face each other at one side of the wedge groove so that a portion between the wedge catching protrusions becomes narrow.

6. The structure of claim 5, wherein the extension is formed to be relatively longer than a length of the core.

7. The structure of claim 1, wherein the outer shells are disposed to overlap one another.

8. The structure of claim 1, wherein a plurality of spacers is further provided on the bolt so that a plurality of cores is installed.

9. The structure of any one of claims 1 to 8 used to connect structural bodies which have a doughnut-shaped cross section and a predetermined inner diameter.

* * * * *